United States Patent
Maghribi et al.

(10) Patent No.: US 7,337,012 B2
(45) Date of Patent: Feb. 26, 2008

(54) STRETCHABLE POLYMER-BASED ELECTRONIC DEVICE

(75) Inventors: Mariam N. Maghribi, Livermore, CA (US); Peter A. Krulevitch, Pleasanton, CA (US); James Courtney Davidson, Livermore, CA (US); Thomas S. Wilson, Castro Valley, CA (US); Julie K. Hamilton, Tracy, CA (US); William J. Benett, Livermore, CA (US); Armando R. Tovar, San Antonio, TX (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 299 days.

(21) Appl. No.: 10/825,787

(22) Filed: Apr. 16, 2004

(65) Prior Publication Data

US 2004/0243204 A1   Dec. 2, 2004

Related U.S. Application Data

(60) Provisional application No. 60/467,000, filed on Apr. 30, 2003.

(51) Int. Cl.
*A61N 1/375* (2006.01)
*A61B 5/0408* (2006.01)
(52) U.S. Cl. ...................... 607/152; 600/393
(58) Field of Classification Search ........ 600/388–390, 600/393; 607/152
See application file for complete search history.

(56) References Cited

U.S. PATENT DOCUMENTS

| | | | |
|---|---|---|---|
| 5,346,850 A | 9/1994 | Kaschmitter et al. | |
| 5,395,481 A | 3/1995 | McCarthy | |
| 5,414,276 A | 5/1995 | McCarthy | |
| 5,817,550 A | 10/1998 | Carey et al. | |
| 6,324,429 B1 | 11/2001 | Shire et al. | |
| 6,337,761 B1* | 1/2002 | Rogers et al. | 359/296 |
| 6,341,504 B1* | 1/2002 | Istook | 66/172 E |
| 2003/0020844 A1* | 1/2003 | Albert et al. | 349/33 |
| 2003/0032946 A1* | 2/2003 | Fishman et al. | 604/890.1 |

\* cited by examiner

*Primary Examiner*—Carl Layno
*Assistant Examiner*—Tammie K Heller
(74) *Attorney, Agent, or Firm*—Eddie E. Scott; John H. Lee

(57) ABSTRACT

A stretchable electronic circuit or electronic device and a polymer-based process to produce a circuit or electronic device containing a stretchable conducting circuit. The stretchable electronic apparatus has a central longitudinal axis and the apparatus is stretchable in a longitudinal direction generally aligned with the central longitudinal axis. The apparatus comprises a stretchable polymer body and at least one circuit line operatively connected to the stretchable polymer body. The circuit line extends in the longitudinal direction and has a longitudinal component that extends in the longitudinal direction and has an offset component that is at an angle to the longitudinal direction. The longitudinal component and the offset component allow the apparatus to stretch in the longitudinal direction while maintaining the integrity of the circuit line.

22 Claims, 3 Drawing Sheets

STRETCHABLE POLYMER-BASED ELECTRONIC DEVICE

CROSS-REFERENCE TO RELATED APPLICATIONS

This application claims the benefit of U.S. Provisional Patent Application No. 60/467,000 filed Apr. 30, 2003 and titled "Stretchable Polymer-Based Conductive Microcable." U.S. Provisional Patent Application No. 60/467,000 filed Apr. 30, 2003 and titled "Stretchable Polymer-Based Conductive Microcable" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to electronic devices and more particularly to a stretchable electronic device.

2. State of Technology

U.S. Pat. No. 5,817,550 for a method for formation of thin film transistors on plastic substrates to Paul G. Carey, Patrick M. Smith, Thomas W. Sigmon, and Randy C. Aceves, issued Oct. 6, 1998, provides the following state of technology information, "Recently a process was developed for crystallizing and doping amorphous silicon on a low cost, so-called low-temperature plastic substrate using a short pulsed high energy source in a selected environment, without heat propagation and build-up in the substrate so as to enable use of plastic substrates incapable of withstanding sustained processing temperatures higher than about 180° C. Such a process is described and claimed in U.S. Pat. No. 5,346,850 issued Sep. 13, 1994 to J. L. Kaschmitter et al., assigned to the Assignee of the instant application. Also, recent efforts to utilize less expensive and lower temperature substrates have been carried out wherein the devices were formed using conventional temperatures on a sacrificial substrate and then transferred to another substrate, with the sacrificial substrate thereafter removed. Such approaches are described and claimed in U.S. Pat. No. 5,395,481 issued Mar. 7, 1995, U.S. Pat. No. 5,399,231 issued Mar. 21, 1995, and U.S. Pat. No. 5,414,276 issued May 9, 1995, each issued to A. McCarthy and assigned to the assignee of the instant application."

U.S. Pat. No. 6,324,429 for a chronically implantable retinal prosthesis by Doug Shire, Joseph Rizzo, and John Wyatt, of the Massachusetts Eye and Ear Infirmary Massachusetts Institute of Technology issued Nov. 27, 2001 provides the following state of technology information, "In the human eye, the ganglion cell layer of the retina becomes a monolayer at a distance of 2.5-2.75 mm from the foveola center. Since the cells are no longer stacked in this outer region, this is the preferred location for stimulation with an epiretinal electrode array. The feasibility of a visual prosthesis operating on such a principle has been demonstrated by Humayun, et al. in an experiment in which the retinas of patients with retinitis pigmentosa, age-related macular degeneration, or similar degenerative diseases of the eye were stimulated using bundles of insulated platinum wire."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a stretchable electronic circuit or electronic device and a polymer-based process to produce a circuit or electronic device containing a stretchable a conducting circuit. The stretchable electronic apparatus has a central longitudinal axis and the apparatus is stretchable in a longitudinal direction generally aligned with the central longitudinal axis. The apparatus comprises a stretchable polymer body and at least one circuit line operatively connected to the stretchable polymer body. The circuit (electrical or fluidic conductive) line extends in the longitudinal direction and has a longitudinal component that extends in the longitudinal direction and has an offset component that is at an angle to the longitudinal direction. The longitudinal component and the offset component allow the apparatus to stretch in the longitudinal direction while maintaining the integrity of the circuit line.

The stretchable electronic circuit or electronic device has particular use in high density electrode device interconnect. As the density of electrodes increases for such applications as epiretinal stimulation there is a need to provide a viable means of making contact to energize and control each individual electrode. These contacts also need to be somewhat stretchable to permit manipulation during surgical implanting. The stretchable electronic circuit or electronic device provides the means to integrate an arbitrary number of conductive traces using a stackable, 3-D array of conductors design in such a way as to provide stress release and increased stretchability.

The invention is susceptible to modifications and alternative forms. Specific embodiments are shown by way of example. It is to be understood that the invention is not limited to the particular forms disclosed. For example, the invention can be used for fluidic circuits as well as electrical circuits. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
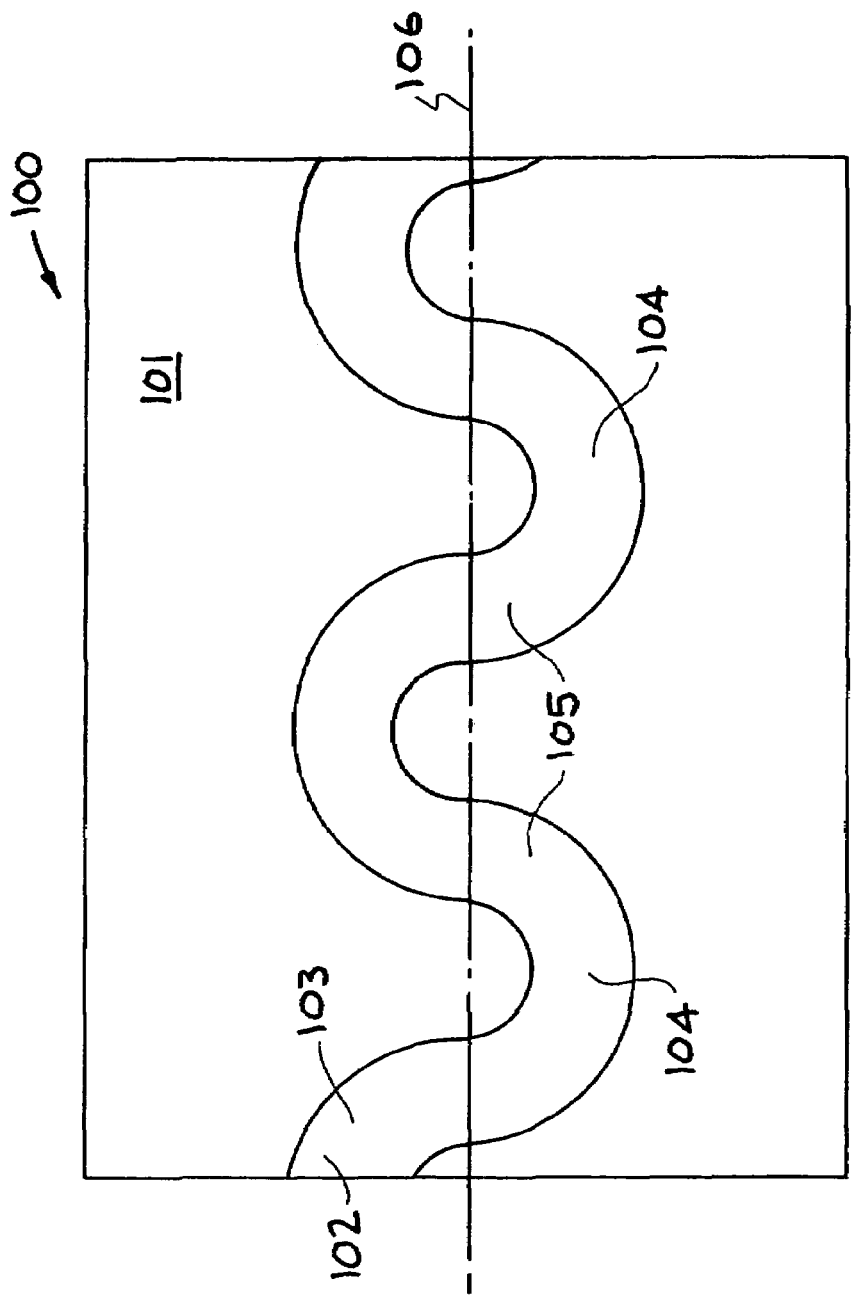
FIG. 1 illustrates an embodiment of a circuit constructed in accordance with the present invention.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to in FIG. 1, an embodiment of an apparatus constructed in accordance with the present invention is illustrated. The apparatus is generally designated by the reference numeral 100. The embodiment 100 provides a stretchable electronic circuit or electronic device 100. The embodiment 100 provides a polymer-based process to produce a circuit or electronic device 100 containing stretchable a conducting line or conductive trace. The embodiment 100 provides a stretchable electronic apparatus 100 having a central longitudinal axis 106 wherein the apparatus 100 is stretchable in a longitudinal direction generally aligned with the central longitudinal axis 106 of the apparatus 100. The apparatus 100 comprises a stretchable polymer body 101 and at least one conducting line or conducting trace line 103 operatively connected to the stretchable polymer body 101. The conducting line or conducting trace line 103 extends in the longitudinal direction and has a longitudinal section 104 that extends in the longitudinal direction and has an offset section 105 that is at an angle to the longitudinal direction. The longitudinal section 104 and the offset section 105 allow the apparatus 100 to stretch in the longitudinal direction while maintaining the integrity of the conducting line or conducting trace line 103.

The conducting line or conducting trace 100 has particular use in high density electrode device interconnect. As the density of electrodes increases for such applications as epiretinal stimulation there is need to provide a viable means of making contact to energize and control each individual electrode. These contacts also need to be somewhat stretchable to permit manipulation during surgical implanting. The system 100 provides the means to integrate an arbitrary number of conductive traces using a stackable, 3-D array of conductors design in such a way as to provide stress release and increased stretchability.

As shown in FIG. 1, the electronic conducting line or conducting trace 100 includes conducting material 103 integrated into a substrate 101. The conducting line or conducting trace 100 is comprised of at least one microchannel 102 that contains electrically conducting media 103. The microchannel 102 containing electrically conducting media 103 includes sections 104 that are aligned with the axis 106 of the conducting line or conducting trace 100 and sections 105 that are at an angle to the axis 106 of the conducting line or conducting trace 100. The sections 105 that are at an angle to the axis 106 of the conducting line or conducting trace 100 allow the conducting line or conducting trace to stretch without losing the ability to conduct and transmit the desired signal.

The system 100 has many uses. One important use is in implantable biomedical microdevice electrode and interconnect formation. Other uses include biocompatible interconnects for a multitude of surgical implants; implantable, biocompatible electrical interconnect cabling; polymer based microelectrodes; polymer-based multilevel and multicomponent systems interconnect; applications requiring flexible and stretchable electrical interconnect; fanout metalization for connectorization of integrated PDMS microsystems; compact, hermetically sealed, high conductor density cabling; flexible and stretchable electrically conducting interconnect for compact consumer electronic products, internal and external medical device interconnect; implantable devices; epiretinal, subretinal, and cortical artificial vision implant, cochlear implants, neurological implants, spinal cord implants and other neural interface implants; implantable and transdermal drug delivery devices; monitoring devices; implantable ribbon cables and electrode array for deep brain stimulation, spinal cord reattachment, nerve regeneration, cortical implants, retinal implants, cochlear implants, drug delivery, muscle stimulation and relaxation; flexible displays and smart notes, conformable circuits; low weight and profile high density conductors for aviation; and insulated interconnect cabling for aquatic applications such as environmental monitoring.

The present invention provides a method of fabricating stretchable, polymer-based electrically conducting traces. The microchannel 102 is produced using a cast molding technique. Photolithography is used to define the microchannel 102 to produce the casting mould. Multiple channels can be fabricated on a single substrate. While channel widths and depths are arbitrary, both dimensions are nominally on the order of a few to 100 µm. Moulds can be reused to produce many single layer substrates containing multiple channels. Each single layer contains open channel conduits comprised of two walls and a bottom. Channels are totally enclosed by bonding the single layer substrates on top of each other. One unique capping substrate is required to encapsulate the last layer channels.

The process yields a 3-D bonded substrate containing at least one microchannel 102 that is subsequently filled with a conductive media such as conductive ink. The microchannel 102 can be filled with using vacuum for lower viscosity conductive inks. Higher viscosity inks require pressure filling techniques. Microchannel conducting cables can be fabricated such that the ends terminate flush in the same plane or they may be stepped to provide open contacts which can be used for interconnection or even serve as exposed electrodes.

The conductive ink 103 contains fine ground metals. Silver and platinum serve as example metals used in conductive inks. Iridium and iridium oxide is an example of another more specialized conductive system noted for biocompatiblity in electrode applications. Many conductive inks are commercially obtainable or can be formulated using a polymer-based carrier material such as silicone or polyester. Each of these example carriers is compatible with the substrate material.

While the process described above can be used to make arbitrary 3-D microconducting trace array cables, the design of the channel shape is important in producing maximally stretchable interconnects. The FIG. 1 conducting line or conducting trace 100 uses a serpentine, S-shaped, channel 102. This structure permits stretching along axis 106 of the channel/conductor 102/103.

The conducting line or conducting trace 100 shown in FIG. 1 and the process described above uses polydimethylsiloxane (PDMS) as the substrate 101. In order for the PDMS substrate 101 to be an ideal, low cost, integration and packaging platform, demonstration of metalization to create the conducting line or conducting trace lines 102/103. The drawings and written description illustrate a number of specific embodiments of the invention. These embodiments and other embodiments give a broad illustration of the invention. Various changes and modifications within the spirit and scope of the invention will become apparent to those skilled in the art.

In one embodiment, Applicants produce three-dimensional microfluidic channels 102 in the PDMS substrate 101. Applicants then fill the microfluidic networks with liquid conductive ink 103. Applicants then cure the ink to produce embedded conducting networks within the PDMS substrate 101. A syringe is used to inject the ink into the channels to allow for an even distribution throughout the structure. Alternatively, a vacuum can be used to draw the ink through the microfluidic network. After the ink is dispersed throughout the channels it is then cured producing conductive micron-scale wires.

The Microfluidic Networks can be produce as described in International Patent No. WO0189787 published Nov. 29, 2001 and May 30, 2002, titled "MICROFLUIDIC SYSTEMS INCLUDING THREE-DIMENSIONALLY ARRAYED CHANNEL NETWORKS," to the President and Fellows of Harvard College invented by Anderson, et al. This patent describes methods for fabricating improved microfluidic systems, which contain one or more levels of microfluidic channels. The microfluidic channels can include three-dimensionally arrayed networks of fluid flow paths therein including channels that cross over or under other channels of the network without physical intersection at the points of cross over. The microfluidic networks of the can be fabricated via replica molding processes. International Patent No. WO0189787 and the information and disclosure provided thereby is incorporated herein by reference.

In another embodiment, applicants produce three-dimensional microfluidic channels in the PDMS substrate 101 using a stamp to place the ink in a desired pattern on layers of PDMS. A description of a deformable stamp for patterning a surface is shown in U.S. patent application No. 2002/0050220 for a deformable stamp for patterning three-dimensional surfaces by Olivier Schueller, Enoch Kim, and George Whitesides published May 5, 2002. U.S. patent application No. 2002/0050220 is incorporated herein by reference.

The stamp can be placed in contact with an entire 3-dimensional object, such as a rod, in a single step. The stamp can also be used to pattern the inside of a tube or rolled over a surface to form a continuous pattern. The stamp may also be used for fluidic patterning by flowing material through channels defined by raised and recessed portions in the surface of the stamp as it contacts the substrate. The stamp may be used to deposit self-assembled monolayers, biological materials, metals, polymers, ceramics, or a variety of other materials. The patterned substrates may be used in a variety of engineering and medical applications. This approach can be used to pattern the conductive inks to produce multi level metalization as follows:

1. An etched substrate of silicon, glass, or comparable type is used to mold the PDMS to a desired pattern. Photoresist or other material can also be patterned onto the silicon or glass substrate to create the mold.
2. The PDMS is applied on the mold, allowed to cure and then peeled away from the substrate forming a stamp.
3. The conductive ink is then spin coated onto a second application wafer to achieve a thin coating.
4. The PDMS stamp is then applied to this wafer allowing for the ink to transfer from the application wafer to the stamp.
5. The PDMS stamp with the ink applied to it is aligned with the PDMS-coated substrate wafer and placed in contact, then removed, transferring the ink.
6. The ink is then allowed to cure at the appropriate temperature for proper adhesion.
7. Once the ink is cured a layer of photoresist is applied and patterned to produce posts that will form the interconnects between metal layers. This is done using photolithography techniques.
8. A second layer of PDMS is applied to the substrate wafer to passivate the first layer of metal without exceeding the height of the photoresist posts.
9. After curing the PDMS, the photoresist posts are removed in acetone, leaving vias down to the underlying metal layer.
10. The holes are filled either by filling with conductive ink or by electroplating.
11. For multi-layer metalization steps 3-11 are repeated until the desired number of levels are achieved.

Another embodiment of a system for creating the conducting line or conducting trace 100 is photolithography. Photoresist is spun onto the substrate wafer and patterned, exposing the underlying PDMS layer in regions where the conductive ink is to be applied. The conductive ink is then spread onto the substrate, either by spin-coating or spraying. After curing, the photoresist is removed in acetone, lifting off the undesired conductive ink. This process can be replicated until the desired levels are completed.

Another embodiment of a system for creating the conducting line or conducting trace 100 is screen printing. To avoid the use of photoresist and the possibility of losing excessive amounts of ink in the photolithography process, the ink can simply be screen printed on using traditional techniques. A permeable screen mesh of either monofilament polyester or stainless steel is stretched across a frame. The frame with a stencil with the desired pattern is placed on top of the wafer with cured PDMS. Using a squeegee the conductive ink is pushed through the stencil and onto the substrate wafer. Another screen mesh with stencil is used to apply the appropriate interconnections for each layer of metalization. After which a second layer of PDMS is applied to the substrate wafer to passivate the first layer of metal without exceeding the height of the metal interconnections. This process is repeated until the desired number of levels is achieved.

Figure 2:
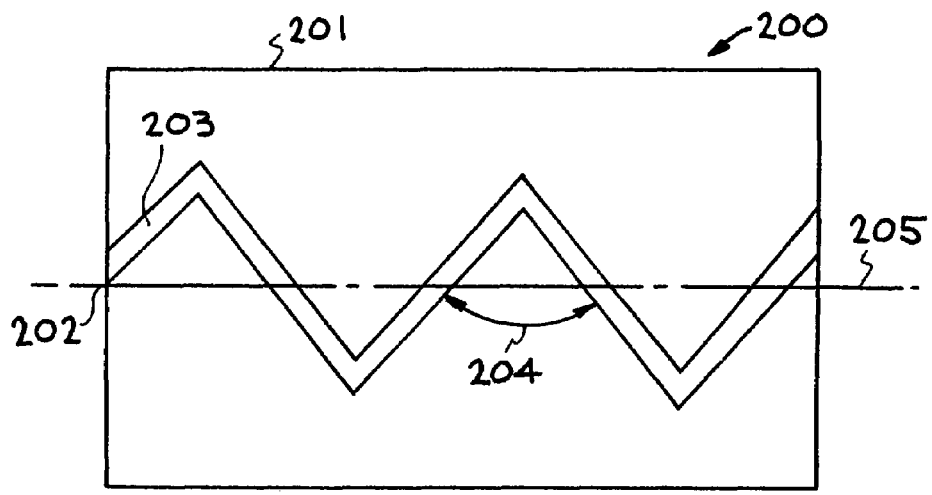
FIG. 2 illustrates another embodiment of a circuit constructed in accordance with the present invention.

Referring now to in FIG. 2, another embodiment of an apparatus constructed in accordance with the present invention is illustrated. The apparatus is generally designated by the reference numeral 200. The embodiment 200 provides a stretchable electronic circuit or electronic device 200. The embodiment 200 provides a polymer-based process to produce a circuit or electronic device 200 containing stretchable conducting circuit 202. The embodiment 200 provides a stretchable electronic apparatus 200 having a central longitudinal axis 205. The apparatus 200 is stretchable in a longitudinal direction generally aligned with the central longitudinal axis 205 of the apparatus 200. The apparatus 200 comprises a stretchable polymer body 201 and at least one circuit 202 operatively connected to the stretchable polymer body 201. The circuit 202 comprises a conducting media 203. The circuit 202 extends in the longitudinal direction and has a longitudinal component that extends in the longitudinal direction and has an offset component that is at an angle to the longitudinal direction. The longitudinal component and the offset component allow the apparatus 200 to stretch in the longitudinal direction while maintaining the integrity of the circuit 202.

The FIG. 2 apparatus 200 provides a zig zag circuit 202 with a longitudinal component that extends in the longitudinal direction and has an offset component that is at an angle to the longitudinal direction. This structure permits stretching along axis 205 of the circuit 202. First principles in mechanics demonstrate that the optimum shape to provide the highest degree of stretching along axis 205 with minimal sheer force is that of a sawtooth with adjacent segments at an angle 204 of 45° to each other.

The apparatus 200 shown in FIG. 2 and the process of making the apparatus 200 utilizes a stretchable polymer substrate 201. The apparatus 200 has particular use in high density electrode device interconnect. As the density of electrodes increases for such applications as epiretinal stimulation there is a need to provide a viable means of making contact to energize and control each individual electrode. These contacts also need to be somewhat stretchable to permit manipulation during surgical implanting. The system 200 provides the means to integrate an arbitrary number of conductive traces using a stackable, 3-D array of conductors design in such a way as to provide stress release and increased stretchability.

As shown in FIG. 2, the electronic apparatus 200 includes conducting material 203 integrated into a substrate 201. The apparatus 200 is comprised of at least one microchannel 202 that contains electrically conducting media 203. The microchannel 202 containing electrically conducting media 203 includes components that are aligned with the axis 205 of the apparatus 200 and components that are at an angle to the axis 205 of the apparatus 200. The components that are aligned and the components that are at an angle to the axis 205 of the apparatus 200 allow the circuit to stretch without losing the ability to conduct and transmit the desired signal.

The system 200 has many uses. One important use is in implantable biomedical microdevice electrode and interconnect formation. Other uses include biocompatible interconnects for a multitude of surgical implants; implantable, biocompatible electrical interconnect cabling; polymer based microelectrodes; polymer-based multilevel and multicomponent systems interconnect; applications requiring flexible and stretchable electrical interconnect; fanout metalization for connectorization of integrated PDMS Microsystems; compact, hermetically sealed, high conductor density cabling; flexible and stretchable electrically conducting interconnect for compact consumer electronic products, internal and external medical device interconnect; implantable devices; epiretinal, subretinal, and cortical artificial vision implant, cochlear implants, neurological implants, spinal cord implants and other neural interface implants; implantable and transdermal drug delivery devices; monitoring devices; implantable ribbon cables and electrode array for deep brain stimulation, spinal cord reattachment, nerve regeneration, cortical implants, retinal implants, cochlear implants, drug delivery, muscle stimulation and relaxation; flexible displays and smart notes, conformable circuits; low weight and profile high density conductors for aviation; and insulated interconnect cabling for aquatic applications such as environmental monitoring.

The present invention provides methods of fabricating stretchable, polymer-based electrically conducting circuits and apparatus. In one embodiment, the microchannel 202 is produced using a cast molding technique. Photolithography is used to define the microchannel 202 to produce the casting mould. Multiple channels can be fabricated on a single substrate. While channel widths and depths are arbitrary, both dimensions are nominally on the order of a few to 100 µm. Moulds can be reused to produce many single layer substrates containing multiple channels. Each single layer contains open channel conduits comprised of two walls and a bottom. Channels are totally enclosed by bonding the single layer substrates on top of each other. One unique capping substrate is required to encapsulate the last layer channels.

The process yields a 3-D bonded substrate containing at least one microchannel 202 that is subsequently filled with a conductive media such as conductive ink. The microchannel 202 can be filled with using vacuum for lower viscosity conductive inks. Higher viscosity inks require pressure filling techniques. Microchannel conducting cables can be fabricated such that the ends terminate flush in the same plane or they may be stepped to provide open contacts which can be used for interconnection or even serve as exposed electrodes.

The conductive material 203 contains fine ground metals. Silver and platinum serve as example metals used in conductive inks. Iridium and iridium oxide is an example of another more specialized conductive system noted for biocompatiblity in electrode applications. Many conductive inks are commercially obtainable or can be formulated using a polymer-based carrier material such as silicone or polyester. Each of these example carriers are compatible with the substrate material.

While the process described above can be used to make arbitrary 3-D microconducting trace array cables, the design of the channel shape is important in producing maximally stretchable interconnects.

Figure 3:
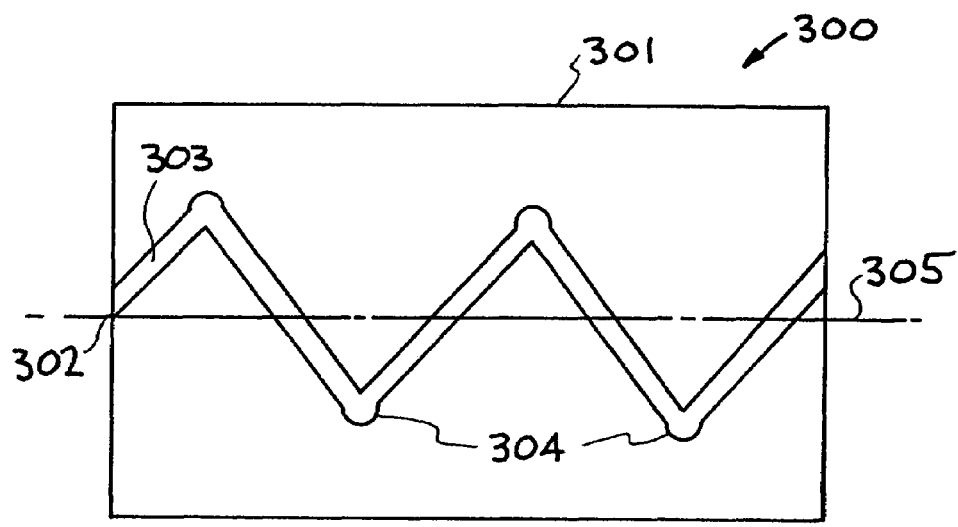
FIG. 3 illustrates another embodiment of a circuit constructed in accordance with the present invention.

Referring now to in FIG. 3, another embodiment of an apparatus constructed in accordance with the present invention is illustrated. The apparatus is generally designated by the reference numeral 300. The embodiment 300 provides a stretchable electronic circuit or electronic device 300. The embodiment 300 provides a polymer-based process to produce a circuit or electronic device 300 containing stretchable conducting circuit 302. The embodiment 300 provides a stretchable electronic apparatus 300 having a central longitudinal axis 305. The apparatus 300 is stretchable in a longitudinal direction generally aligned with the central longitudinal axis 305 of the apparatus 300. The apparatus 300 comprises a stretchable polymer body 301 and at least one circuit 302 operatively connected to the stretchable polymer body 301. The circuit 302 comprises a conducting media 303. The circuit 302 extends in the longitudinal direction and has a longitudinal component that extends in the longitudinal direction and has an offset component that is at an angle to the longitudinal direction. The longitudinal component and the offset component allow the apparatus 300 to stretch in the longitudinal direction while maintaining the integrity of the circuit 302.

The FIG. 3 circuit 300 provides a zig zag circuit 302 with a longitudinal component that extends in the longitudinal direction and has an offset component that is at an angle to the longitudinal direction. This structure permits stretching along axis 305 of the circuit 302. The circuit 302 is a sawtooth shape. The corners 304 of the sawteeth are rounded to induce rotational translation of the conductors to reduce strain when stretched.

The circuit 300 shown in FIG. 3 and the process described above uses polydimethylsiloxane (PDMS) as the substrate 301. In order for the PDMS substrate 301 to be an ideal, low cost, integration and packaging platform, demonstration of metalization to create the circuit lines 302/303. The drawings and written description illustrate a number of specific embodiments of the invention. These embodiments and other embodiments give a broad illustration of the invention. Various changes and modifications within the spirit and scope of the invention will become apparent to those skilled in the art.

In one embodiment, Applicants produce three-dimensional microfluidic channels 302 in the PDMS substrate 301. Applicants then fill the microfluidic networks with liquid conductive ink 303. Applicants then cure the ink to produce embedded conducting networks within the PDMS substrate 301. A syringe is used to inject the ink into the channels to allow for an even distribution throughout the structure. Alternatively, a vacuum can be used to draw the ink through the microfluidic network. After the ink is dispersed throughout the channels it is then cured producing conductive micron-scale wires.

The Microfluidic Networks can be produce as described in International Patent No. WO0189787 published Nov. 29, 2001 and May 30, 2002, titled "MICROFLUIDIC SYSTEMS INCLUDING THREE-DIMENSIONALLY ARRAYED CHANNEL NETWORKS," to the President and Fellows of Harvard College invented by Anderson, et al. This patent describes methods for fabricating improved microfluidic systems, which contain one or more levels of microfluidic channels. The microfluidic channels can include three-dimensionally arrayed networks of fluid flow paths therein including channels that cross over or under other channels of the network without physical intersection at the points of cross over. The microfluidic networks of the can be fabricated via replica molding processes. International Patent No. WO0189787 and the information and disclosure provided thereby is incorporated herein by reference.

In another embodiment, applicants produce three-dimensional microfluidic channels in the PDMS substrate 301 using a stamp to place the ink in a desired pattern on layers of PDMS. A description of a deformable stamp for patterning a surface is shown in U.S. patent application No. 2002/0050220 for a deformable stamp for patterning three-dimensional surfaces by Olivier Schueller, Enoch Kim, and George Whitesides published May 5, 2002. U.S. patent application No. 2002/0050220 is incorporated herein by reference.

The stamp can be placed in contact with an entire 3-dimensional object, such as a rod, in a single step. The stamp can also be used to pattern the inside of a tube or rolled over a surface to form a continuous pattern. The stamp may also be used for fluidic patterning by flowing material through channels defined by raised and recessed portions in the surface of the stamp as it contacts the substrate. The stamp may be used to deposit self-assembled monolayers, biological materials, metals, polymers, ceramics, or a variety of other materials. The patterned substrates may be used in a variety of engineering and medical applications. This approach can be used to pattern the conductive inks to produce multi level metalization as follows:

1. An etched substrate of silicon, glass, or comparable type is used to mold the PDMS to a desired pattern. Photoresist or other material can also be patterned onto the silicon or glass substrate to create the mold.
2. The PDMS is applied on the mold, allowed to cure and then peeled away from the substrate forming a stamp.
3. The conductive ink is then spin coated onto a second application wafer to achieve a thin coating.
4. The PDMS stamp is then applied to this wafer allowing for the ink to transfer from the application wafer to the stamp.
5. The PDMS stamp with the ink applied to it is aligned with the PDMS-coated substrate wafer and placed in contact, then removed, transferring the ink.
6. The ink is then allowed to cure at the appropriate temperature for proper adhesion.
7. Once the ink is cured a layer of photoresist is applied and patterned to produce posts that will form the interconnects between metal layers. This is done using photolithography techniques.
8. A second layer of PDMS is applied to the substrate wafer to passivate the first layer of metal without exceeding the height of the photoresist posts.
9. After curing the PDMS, the photoresist posts are removed in acetone, leaving vias down to the underlying metal layer.
10. The holes are filled either by filling with conductive ink or by electroplating.
11. For multi-layer metalization steps 3-11 are repeated until the desired number of levels are achieved.

Another embodiment of a system for creating the circuit 300 is photolithography. Photoresist is spun onto the substrate wafer and patterned, exposing the underlying PDMS layer in regions where the conductive ink is to be applied. The conductive ink is then spread onto the substrate, either by spin-coating or spraying. After curing, the photoresist is removed in acetone, lifting off the undesired conductive ink. This process can be replicated until the desired levels are completed.

Another embodiment of a system for creating the circuit 300 is screen printing. To avoid the use of photoresist and the possibility of losing excessive amounts of ink in the photolithography process, the ink can simply be screen printed on using traditional techniques. A permeable screen mesh of either monofilament polyester or stainless steel is stretched across a frame. The frame with a stencil with the desired pattern is placed on top of the wafer with cured PDMS. Using a squeegee the conductive ink is pushed through the stencil and onto the substrate wafer. Another screen mesh with stencil is used to apply the appropriate interconnections for each layer of metalization. After which a second layer of PDMS is applied to the substrate wafer to passivate the first layer of metal without exceeding the height of the metal interconnections. This process is repeated until the desired number of levels is achieved.

The circuit 300 has particular use in high density electrode device interconnect. As the density of electrodes increases for such applications as epiretinal stimulation there is a need to provide a viable means of making contact to energize and control each individual electrode. These contacts also need to be somewhat stretchable to permit manipulation during surgical implanting. The system 300 provides the means to integrate an arbitrary number of conductive traces using a stackable, 3-D array of conductors design in such a way as to provide stress release and increased stretchability.

As shown in FIG. 3, the electronic circuit 300 includes conducting material 303 integrated into a substrate 301. The circuit 300 is comprised of at least one microchannel 302 that contains electrically conducting media 303. The microchannel 302 containing electrically conducting media 303 includes components that are aligned with the axis 305 of the circuit 300 and components that are at an angle to the axis 305 of the circuit 300. The components that are at an angle to the axis 305 of the circuit 300 allow the circuit to stretch without losing the ability to conduct and transmit the desired signal.

The system 300 has many uses. One important use is in implantable biomedical microdevice electrode and interconnect formation. Other uses include biocompatible interconnects for a multitude of surgical implants; implantable, biocompatible electrical interconnect cabling; polymer based microelectrodes; polymer-based multilevel and multicomponent systems interconnect; applications requiring flexible and stretchable electrical interconnect; fanout metalization for connectorization of integrated PDMS microsystems; compact, hermetically sealed, high conductor density cabling; flexible and stretchable electrically conducting interconnect for compact consumer electronic products, internal and external medical device interconnect; implantable devices; epiretinal, subretinal, and cortical artificial vision implant, cochlear implants, neurological implants, spinal cord implants and other neural interface implants; implantable and transdermal drug delivery devices; monitoring devices; implantable ribbon cables and electrode array for deep brain stimulation, spinal cord reattachment, nerve regeneration, cortical implants, retinal implants, cochlear implants, drug delivery, muscle stimulation and relaxation; flexible displays and smart notes, conformable circuits. Low weight and profile high density conductors for aviation; and insulated interconnect cabling for aquatic applications such as environmental monitoring.

The present invention provides a method of fabricating stretchable, polymer-based electrically conducting traces. The microchannel 302 is produced using a cast molding technique. Photolithography is used to define the microchannel 302 to produce the casting mould. Multiple channels can be fabricated on a single substrate. While channel widths and depths are arbitrary, both dimensions are nominally on the order of a few to 100 μm. Moulds can be reused to produce many single layer substrates containing multiple channels. Each single layer contains open channel conduits comprised of two walls and a bottom. Channels are totally enclosed by bonding the single layer substrates on top of each other. One unique capping substrate is required to encapsulate the last layer channels.

The process yields a 3-D bonded substrate containing at least one microchannel 302 that is subsequently filled with a conductive media such as conductive ink. The microchannel 302 can be filled with using vacuum for lower viscosity conductive inks. Higher viscosity inks require pressure filling techniques. Microchannel conducting cables can be fabricated such that the ends terminate flush in the same plane or they may be stepped to provide open contacts which can be used for interconnection or even serve as exposed electrodes.

The conductive ink 303 contains fine ground metals. Silver and platinum serve as example metals used in conductive inks. Iridium and iridium oxide is an example of another more specialized conductive system noted for biocompatiblity in electrode applications. Many conductive inks are commercially obtainable or can be formulated using a polymer-based carrier material such as silicone or polyester. Each of these example carriers are compatible with the substrate material.

While the process described above can be used to make arbitrary 3-D microconducting trace array cables, the design of the channel shape is important in producing maximally stretchable interconnects.

Figure 4:
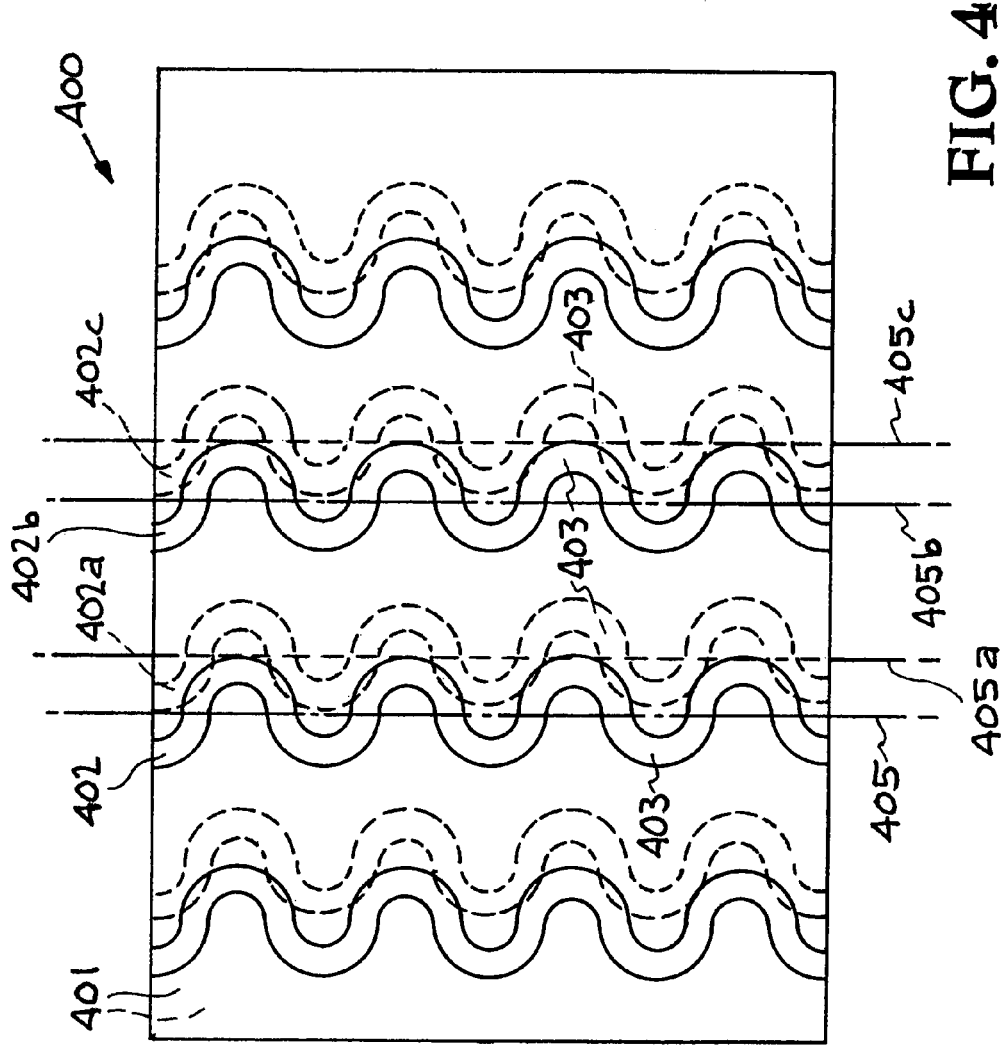
FIG. 4 illustrates another embodiment of a circuit constructed in accordance with the present invention.

Referring now to FIG. 4, an embodiment of an apparatus constructed in accordance with the present invention is illustrated. The apparatus is generally designated by the reference numeral 400. The embodiment 400 provides a stretchable electronic microcable 400. The embodiment 400 provides a polymer-based process to produce a microcable 400 containing stretchable a conducting circuits 402, 402A, 402B, and 402C. The embodiment 400 provides a stretchable microcable 400 having circuits 402, 402A, 402B, and 402C with central longitudinal axes 405, 405A, 405B, and 405C respectively. The microcable 400 is stretchable in a longitudinal direction generally aligned with the central longitudinal axes 405, 405A, 405B, and 405C.

The microcable 400 comprises a stretchable polymer body 401 and multiple circuit lines 402, 402A, 402B, and 402C operatively connected to the stretchable polymer body 401. The circuit lines 402, 402A, 402B, and 402C extend in the longitudinal direction and have longitudinal sections that extends in the longitudinal direction and have offset sections that are at an angle to the longitudinal direction. The longitudinal sections and the offset sections allow the microcable 400 to stretch in the longitudinal direction while maintaining the integrity of the circuit lines 402, 402A, 402B, and 402C.

As shown in FIG. 4, the microcable 400 includes conducting material 403 integrated into the substrate 401. The circuit 400 is comprised of circuit lines 402, 402A, 402B, and 402C that comprise electrically conducting media 403. The circuit lines 402, 402A, 402B, and 402C containing electrically conducting media 403 includes sections that are aligned with the axes 405, 405A, 405B, and 405C of the circuit lines 402, 402A, 402B, and 402C and sections that are at an angle to the axes of the circuit lines 402, 402A, 402B, and 402C. The sections that are at an angle to the axes 405, 405A, 405B, and 405C allow the microcable 400 to stretch without losing the ability to conduct and transmit the desired signal.

Figure 5:
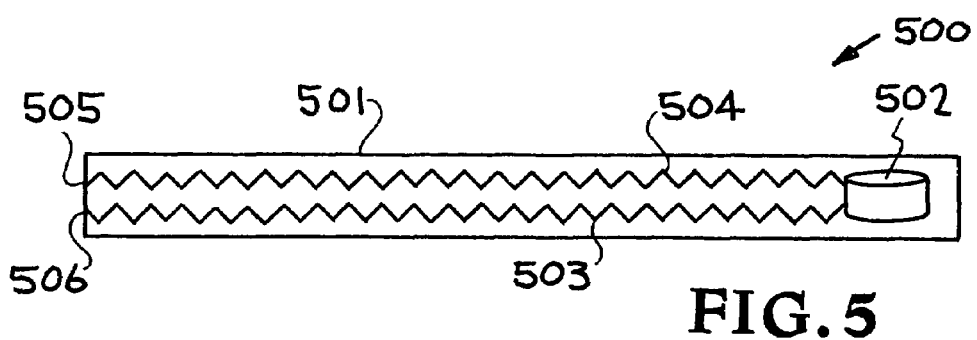
FIG. 5 illustrates an embodiment of an electronic apparatus constructed in accordance with the present invention.

Referring now to in FIG. 5, an embodiment of an electronic apparatus constructed in accordance with the present invention is illustrated. The electronic apparatus is generally designated by the reference numeral 500. The embodiment 500 provides a stretchable electronic device 500. The electronic device 500 comprises a stretchable circuit 503/504 and an electronic component 502.

The electronic device 500 has many uses. For example the electronic device 500 can be used as a MEMS sensor. MEMS or MicroElectroMechanical Systems are known as systems that contain extremely small mechanical elements, often integrated together with electronic processing circuitry. MEMS have feature sizes that are typically measured in micrometers (microns), that is, millionths of a meter. As a reference, the diameter of human hair is about 100 microns. MEMS sensors have a wide variety of applications. For example uses of MEMS sensors include detecting movement, detecting sound, gyroscopes, accelerometers, micro-optical systems, fiber-optic communications, superfast electrophoresis systems for DNA separation, video projection chips, magnetometers, micro-robots, micro-tweezers, neural probes, and many other uses. MEMS sensors are used to detect automobile collisions and deploy airbags, and magnetometers that can detect the presence of military equipment such as tanks, trucks or even a soldier. The electronic apparatus 500 has other uses. The other uses include: an implantable medical device, radio, recorder, recorder and player, video camera, video player, video recorder, video recorder and player, cell phone, computer, calculator, phone tap, device that detects phone taps, audio surveillance device, medical device, biosensor, radiation monitor, which include components such as a power source, battery, solar cell, wireless electronics for communication, capacitor, resistor, inductor, transformer, integrated circuit, microprocessor, digital to analog converter, display, camera, cell phone, and other electronic devices. Discrete components such as batteries, solar cells, displays and microprocessors can be integrated together to form the electronic systems.

The embodiment 500 provides a polymer-based process to produce an electronic device 500 containing stretchable a conducting circuit 503/504 and an electronic component 502. The embodiment 500 provides a stretchable electronic apparatus 500 having a central longitudinal axis wherein the apparatus 500 is stretchable in a longitudinal direction generally aligned with the central longitudinal axis of the electronic apparatus 500. The electronic apparatus 500 comprises a stretchable polymer body 501 and at least one circuit 503/504 operatively connected to the stretchable polymer body 501. The circuit lines 503 and 504 extends in the longitudinal direction and have longitudinal sections that extends in the longitudinal direction and an offset sections that are at an angle to the longitudinal direction. The longitudinal sections and the offset sections allow the apparatus 500 to stretch in the longitudinal direction while maintaining the integrity of the circuit lines 503 and 504 and the electronic component 502.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A stretchable electronic circuit, the circuit having a central longitudinal axis and the circuit being stretchable in a longitudinal direction generally aligned with the central longitudinal axis, comprising:
   a solid stretchable polymer body made entirely of poly(dimethylsiloxane), said solid stretchable polymer body made entirely of poly(dimethylsiloxane) having a polymer body longitudinal axis that is concurrent with the central longitudinal axis of the circuit,
   at least one microchannel in said solid stretchable polymer body made entirely of poly(dimethylsiloxane), said at least one microchannel having a microchannel longitudinal axis that is concurrent with the central longitudinal axis of the circuit, wherein said at least one microchannel extends fully along said microchannel longitudinal axis,
   a multiplicity of microchannel longitudinal components that extend in the longitudinal direction, and
   a multiplicity of micro channel offset components that are at an angle to the longitudinal direction, and
   an electrically conductive media contained in said at least one microchannel,
   wherein said at least one microchannel and said electrically conductive media form an electronic circuit line that extends fully along said microchannel longitudinal axis and is operatively connected to said solid stretchable polymer body made entirely of poly(dimethylsiloxane), said at least one electronic circuit line extending in the longitudinal direction and having
   a multiplicity of circuit line longitudinal components that extend in the longitudinal direction, wherein said multiplicity of circuit line longitudinal components include said multiplicity of microchannel longitudinal components and having
   a multiplicity of circuit line offset components that extend at an angle to the longitudinal direction, wherein said multiplicity of circuit line offset components include said multiplicity of microchannel offset components,
   said circuit line longitudinal component and said circuit line offset component allowing the circuit to stretch in the longitudinal direction while maintaining the integrity of said at least one circuit line.

2. The stretchable electronic circuit of claim 1 wherein said circuit line is S-shaped.

3. The stretchable electronic circuit of claim 1 wherein said circuit line is sawtooth shaped.

4. The stretchable electronic circuit of claim 1 wherein said circuit line is sawtooth shaped with the sawtooth having adjacent segments and said adjacent segments are at an angle of 45° to each other.

5. The stretchable electronic circuit of claim 1 wherein said circuit line is sawtooth shaped with the sawtooth having rounded corners.

6. The stretchable electronic circuit of claim 1 wherein said circuit line is in the form of a serpentine channel.

7. The stretchable electronic circuit of claim 1 wherein said solid stretchable polymer body made entirely of poly(dimethylsiloxane) comprises cast poly(dimethylsiloxane).

8. The stretchable electronic circuit of claim 1 wherein said electrically conductive media comprises electrically conductive ink.

9. The stretchable electronic circuit of claim 1 wherein said solid stretchable polymer body made entirely of poly(dimethylsiloxane) comprises a microcable made entirely of poly(dimethylsiloxane).

10. A stretchable electronic circuit, the circuit having a central longitudinal axis, comprising:
   a solid stretchable and flexible polymer body made entirely of poly(dimethylsiloxane), said solid stretchable and flexible polymer body made entirely of poly(dimethylsiloxane) having a polymer body longitudinal axis that is concurrent with the central longitudinal axis of the circuit,
   at least one microchannel in said solid stretchable polymer body made entirely of poly(dimethylsiloxane), said at least one microchannel having a microchannel longitudinal axis that is concurrent with the central longitudinal axis of the circuit, wherein said at least one microchannel extends fully along said microchannel longitudinal axis,
   a multiplicity of microchannel longitudinal components that extend in the longitudinal direction, and
   a multiplicity of micro channel offset components that are at an angle to the longitudinal direction, and
   an electrically conductive media contained in said at least one microchannel,
   wherein said at least one microchannel and said electrically conductive media form an electronic circuit line that extends fully along said microchannel longitudinal axis and is operatively connected to said flexible polymer substrate, said at least one electronic circuit line having
   a multiplicity of longitudinal components that are aligned with the central longitudinal axis of the circuit, wherein said multiplicity of longitudinal components include said multiplicity of microchannel longitudinal components, and a multiplicity of offset components that are offset from the central longitudinal axis of the circuit, wherein said multiplicity of offset components include said multiplicity of microchannel offset components, and wherein said longitudinal components and said offset components allow the circuit to stretch in the longitudinal direction while maintaining the integrity of said at least one circuit line.

11. The stretchable electronic circuit of claim 10 wherein said at least one circuit line is S-shaped.

12. The stretchable electronic circuit of claim 10 wherein said at least one circuit line is sawtooth shaped.

13. The stretchable electronic circuit of claim 10 wherein said at least one circuit line is sawtooth shaped with the sawtooth having adjacent segments and said adjacent segments are at an angle of 45° to each other.

14. The stretchable electronic circuit of claim 10 wherein said at least one circuit line is sawtooth shaped with the sawtooth having rounded corners.

15. The stretchable electronic circuit of claim 10 wherein said at least one circuit line is in the form of a serpentine channel.

16. The stretchable electronic circuit of claim 10 wherein said solid flexible polymer body made entirely of poly(dimethylsiloxane) comprises cast poly(dimethylsiloxane).

17. The stretchable electronic circuit of claim 10 wherein said electrically conductive media comprises electrically conductive ink.

18. A method of producing a stretchable electronic circuit having a central longitudinal axis and being stretchable in a longitudinal direction generally aligned with the central longitudinal axis, comprising the steps of:
   providing a solid stretchable polymer body made entirely of poly(dimethylsiloxane),
   assuring that said solid stretchable polymer body made entirely of poly(dimethylsiloxane) has a polymer body longitudinal axis that is concurrent with the central longitudinal axis of the electronic circuit;
   providing at least one microchannel in said solid stretchable polymer body made entirely of poly(dimethylsiloxane) with said at least one microchannel having a microchannel longitudinal axis that is concurrent with the central longitudinal axis of the circuit, wherein said at least one microchannel extends fully along said microchannel longitudinal axis,
   a multiplicity of microchannel longitudinal components that extend in the longitudinal direction, and
   a multiplicity of micro channel offset components that are at an angle to the longitudinal direction, and
   filling said at least one microchannel with an electrically conductive media to assure that
   said stretchable polymer body has multiplicity of circuit line longitudinal components that extend in the longitudinal direction, wherein said multiplicity of circuit line longitudinal components include said multiplicity of microchannel longitudinal components and
   said stretchable polymer body has a multiplicity of circuit line offset components that extend at an angle to the longitudinal direction, wherein said multiplicity of circuit line offset components include said multiplicity of microchannel offset components,
   said longitudinal component and said offset component allowing the circuit to stretch in the longitudinal direction while maintaining the integrity of said circuit line longitudinal component and said circuit line offset component.

19. The method of claim 18 wherein said step of providing a solid stretchable polymer body made entirely of poly(dimethylsiloxane) comprises casting a solid stretchable polymer body made entirely of poly(dimethylsiloxane).

20. The method of claim 18 wherein said steps of providing at least one microchannel in said solid stretchable polymer body and filling said at least one microchannel with an electrical conductive media comprises using a stamp to place a conductive ink in a desired pattern on said stretchable polymer body.

21. The method of claim 18 wherein said steps of providing at least one microchannel in said solid stretchable polymer body and filling said at least one microchannel with an electrical conductive media comprises using photolithography.

22. The method of claim 18 wherein said step of providing a solid stretchable polymer body comprises providing a solid micro cable made entirely of poly(dimethylsiloxane).

* * * * *